(12) United States Patent
Sando et al.

(10) Patent No.: US 7,909,063 B2
(45) Date of Patent: Mar. 22, 2011

(54) MICROCHIP INSPECTION SYSTEM AND PROGRAM EMPLOYED FOR THE SAME

(75) Inventors: Yasuhiro Sando, Hyogo (JP); Akihisa Nakajima, Tokyo (JP); Kusunoki Higashino, Osaka (JP); Youichi Aoki, Tokyo (JP)

(73) Assignee: Konica Minolta Medical & Graphic, Inc. (JP)

( * ) Notice: Subject to any disclaimer, the term of this patent is extended or adjusted under 35 U.S.C. 154(b) by 376 days.

(21) Appl. No.: 11/938,464

(22) Filed: Nov. 12, 2007

(65) Prior Publication Data

US 2008/0115598 A1    May 22, 2008

(30) Foreign Application Priority Data

Nov. 17, 2006   (JP) .................................. 2006-311247

(51) Int. Cl.
 *F15C 1/04* (2006.01)
(52) U.S. Cl. ....................................... 137/828; 137/334
(58) Field of Classification Search .................. 137/334, 137/455, 468, 828; 73/865.8
See application file for complete search history.

(56) References Cited

U.S. PATENT DOCUMENTS

| | | | | |
|---|---|---|---|---|
| 3,677,275 A | * | 7/1972 | Lovelock | 137/13 |
| 4,248,086 A | * | 2/1981 | Zizine | 73/861.09 |
| 2002/0008032 A1 | * | 1/2002 | Hayenga | 204/603 |

FOREIGN PATENT DOCUMENTS

| | | |
|---|---|---|
| JP | 2001-322099 | 11/2001 |
| JP | 2004-28589 | 1/2004 |
| JP | 2004-270537 | 9/2004 |
| JP | 2006-149379 | 6/2006 |

* cited by examiner

*Primary Examiner* — Stephen Hepperle
*Assistant Examiner* — William McCalister
(74) *Attorney, Agent, or Firm* — Cantor Colburn LLC

(57) ABSTRACT

There is described a microchip inspection system, which makes it possible not only to correct the influence of the viscosity change of the liquid, but also to accurately conduct the liquid conveyance controlling operation. The microchip inspection system includes: a micro pump to inject a driving liquid from a liquid flow path into a microchip; a liquid temperature adjusting section to adjust a liquid temperature of the driving liquid; a driving liquid detecting section to detect presence or absence of the driving liquid at two predetermined positions located in the liquid flow path, so as to output detection signals; a fluid velocity calculating section to calculate a fluid velocity based on the detection signals outputted by the driving liquid detecting section; and a liquid temperature controlling section to control the liquid temperature adjusting section, based on the fluid velocity calculated by the fluid velocity calculating section.

4 Claims, 12 Drawing Sheets

FIG. 3 (a-1)
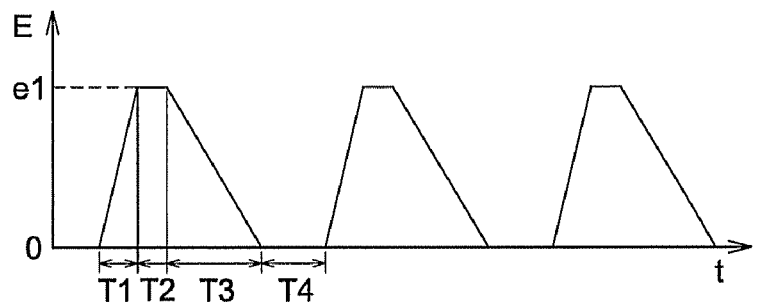
FIG. 3 (a-2)
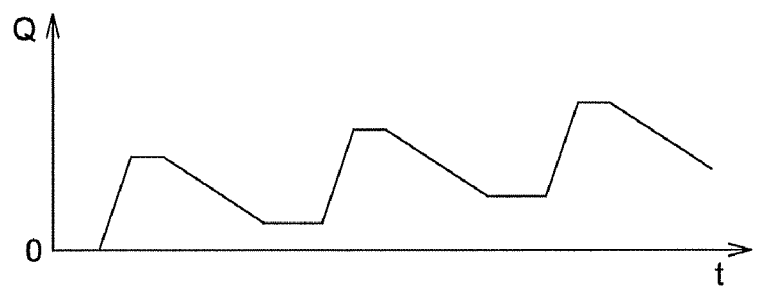
FIG. 3 (b-1)
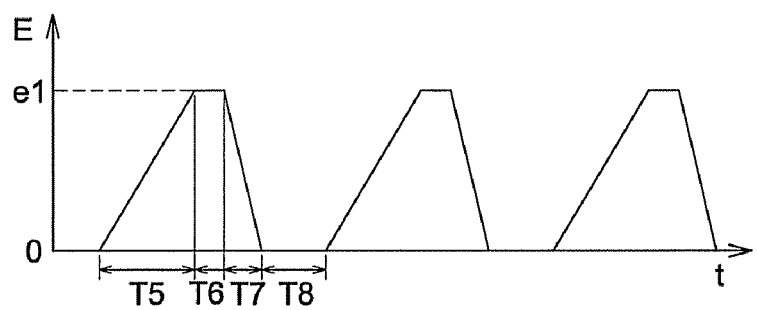
FIG. 3 (b-2)
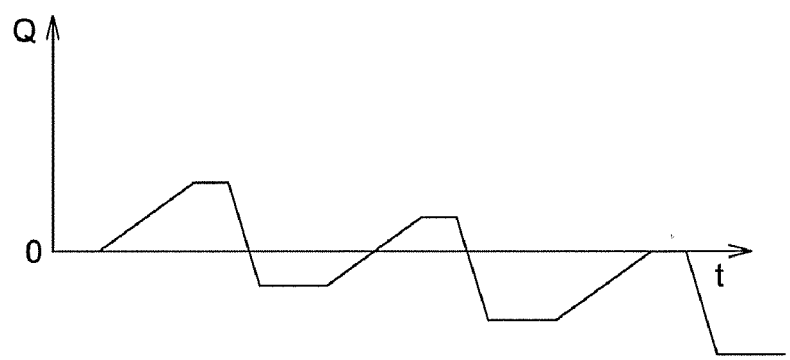

MICROCHIP INSPECTION SYSTEM AND PROGRAM EMPLOYED FOR THE SAME

This application is based on Japanese Patent Application NO. 2006-311247 filed on Nov. 17, 2006 with Japan Patent Office, the entire content of which is hereby incorporated by reference.

BACKGROUND OF THE INVENTION

The present invention relates to a microchip inspection system and a program to be employed for such the microchip inspection system.

In recent years, due to the use of micro-machine technology and microscopic processing technology, systems are being developed in which devices and means (for example pumps, valves, flow paths, sensors or the like) for performing conventional sample preparation, chemical analysis, chemical synthesis and the like are caused to be ultra-fine and integrated on a single chip (for instance, set forth in Tokkai 2004-28589, Japanese Non-Examined Patent Publication). These systems are called µ-TAS (Micro Total Analysis System), bioreactor, lab-on-chips, and biochips, and much is expected of their application in the fields of medical testing and diagnosis, environmental measurement and agricultural manufacturing. In reality, as seen in gene screening, in the case where complicated steps, skilful operations, and machinery operations are necessary, a microanalysis system which is automatic, has high speed and is simple is very beneficial not only in terms of reduction in cost, required amount of sample and required time, but also in terms of the fact that it makes analysis possible in cases where time and place cannot be selected.

For each type of analysis or inspection, since quantitativeness, analysis accuracy, economic efficiency on these analysis chips are considered as important, the task at hand is to ensure a feeding system which has a simple structure and is highly reliable. A micro fluid control element which has high accuracy and excellent reliability is needed. The inventors of this invention have already proposed a suitable micro-pump system and a control method thereof (for instance, set forth in Tokkai 2001-322099, Japanese Non-Examined Patent Publication).

Further, the inventors of this invention have already proposed a liquid flow path constituting a reacting section in which a reagent, etc. is sealed into a fine liquid flow path of the microchip, and a liquid is injected into the fine liquid flow path by employing a micro pump to move the reagent, etc., and a reaction detecting device, which makes it possible to measure a reaction result by successively flowing it into a liquid flow path constituting a detecting section (for instance, set forth in Tokkai 2006-149379, Japanese Non-Examined Patent Publication). In such the reaction detecting device as mentioned in the above, various kinds of liquid conveyance controlling operations, including an operation for controlling a timing of injecting a driving liquid by employing the micro pump unit having plural micro pumps and feeding the driving liquid into a predetermined portion located within the microchip, an amount of the liquid, a rate of the liquid amount change, a conveying direction, etc., are conducted.

However, since the viscosity of the liquid varies with the temperature change of the liquid, sometimes, it has become impossible to conduct the predetermined liquid conveying operation, due to errores in the liquid conveyance controlling operations, such as the timing of injecting the driving liquid by employing the micro pump, the amount of the liquid, the rate of the liquid amount change, etc., which are caused by the temperature changes.

To solve the abovementioned problems, the inventors of this invention have already proposed a method, in which correction talbles corresponding to various kinds of temperatures are provided in advance; a sensor for measuring an environment temperature is eqipped; and the correction talbles are referred on the basis of the temperature measured by the sensor so as to control a voltage for driving the micro pump (for instance, set forth in Tokkai 2004-270537, Japanese Non-Examined Patent Publication).

However, even if the environment temperature is measured by the sensor as set forth in Tokkai 2004-270537, since the environment temperature measured by the sensor and the liquid temperature of the driving liquid residing within the micro pump do not necessary coincide with each other, some error is liable to occur. On the other hand, since an inside area of the micro pump is a microscopic area, it is quite difficult to directly measure the liquid temperature of the driving liquid residing within the micro pump. Further, in the correction method, which employs the correction tabels, it is necessary to prepare a large number of various kinds of the temperature-condition correction tabels in order to suffciently correct the changes of the viscosity of the liquid due to the temperature changes. Since it is difficult to prepare such the various kinds of correction tabels corresponding to various conditions, and it also takes much time to conduct the controlling operations based on such the correction tabels, sometimes, it has become impossible to control the liquid transportation amount of the micro pump within a predetermined range. Accordingly, in the method set forth in Tokkai 2004-270537, since the temperature changes cause errores in the liquid conveyance controlling operations, such as the timing of feeding the driving liquid into a predetermined portion located within the microchip, the amount of the liquid, the rate of the liquid amount change, etc., sometimes, it has become impossible to conduct the predetermined liquid conveying operation.

SUMMARY OF THE INVENTION

To overcome the abovementioned drawbacks in conventional microchip inspection systems, it is one of objects of the present invention to provide a microchip inspection system and a program employed for a microchip inspection system, each of which makes it possible not only to correct the influence of the viscosity change of the liquid, but also to accurately conduct the liquid conveyance controlling operation.

Accordingly, at least one of the objects of the present invention can be attained by microchip inspection systems and a computer readable medium described as follows.

(1) According to a microchip inspection system reflecting an aspect of the present invention, the microchip inspection system comprises: a micro pump to inject a driving liquid from a liquid flow path into a microchip; a liquid temperature adjusting section to adjust a liquid temperature of the driving liquid; a driving liquid detecting section to detect presence or absence of the driving liquid at two predetermined positions located in the liquid flow path, so as to output detection signals; a fluid velocity calculating section to calculate a fluid velocity based on the detection signals outputted by the driving liquid detecting section; and a liquid temperature controlling section to control the liquid temperature adjusting section, based on the fluid velocity calculated by the fluid velocity calculating section.

(2) According to another aspect of the present invention, in the microchip inspection system recited in item 1, the microchip inspection system further comprises: a driving liquid tank to store the driving liquid; and the driving liquid tank is equipped with the liquid temperature adjusting section.

(3) According to still another aspect of the present invention, in the microchip inspection system recited in item 1, the driving liquid detecting section is provided with: a light emitting section to irradiate light onto the liquid flow path in a direction orthogonal to the liquid flow path; a light receiving section to receive the light, irradiate by the light emitting section and penetrating through the liquid flow path, and to generate a signal corresponding to an amount of the light received; and a detecting section to compare the signal generated by the light receiving section with a predetermined value, so as to output the detection signal.

(4) According to yet another aspect of the present invention, in the microchip inspection system recited in item 1, the driving liquid detecting section is provided with: a pair of electrodes disposed inside the liquid flow path; and a detecting section to compare an electric signal, representing an electric current flowing between the pair of electrodes, with a predetermined value, so as to output the detection signal.

(5) According to a computer readable medium reflecting another aspect of the present invention, the computer readable medium storing a computer executable program for controlling a driving liquid to be introduced into a microchip, the program comprising program code for causing a computer to perform the steps of: detecting presence or absence of the driving liquid by employing driving-liquid detecting devices disposed at two predetermined positions located in a mid-course of a liquid flow path led to the microchip, so as to output detection signals, before injecting the driving liquid into the microchip; calculating a fluid velocity of the driving liquid currently flowing into the liquid flow path, based on the detection signals outputted in the detecting step; controlling a liquid temperature adjusting section to adjust a liquid temperature of the driving liquid, based on the fluid velocity calculated in the calculating step; and injecting the driving liquid, the liquid temperature of which is adjusted by the liquid temperature adjusting section in the controlling step, into the microchip.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 3(a-1), FIG. 3(a-2), FIG. 3(b-1) and FIG. 3(b-2) show explanatory graphs for explaining relationships between a driving voltage E to be applied to a piezoelectric element and a liquid flow amount Q;

DETAILED DESCRIPTION OF THE PREFERRED EMBODIMENT

Figure 1:
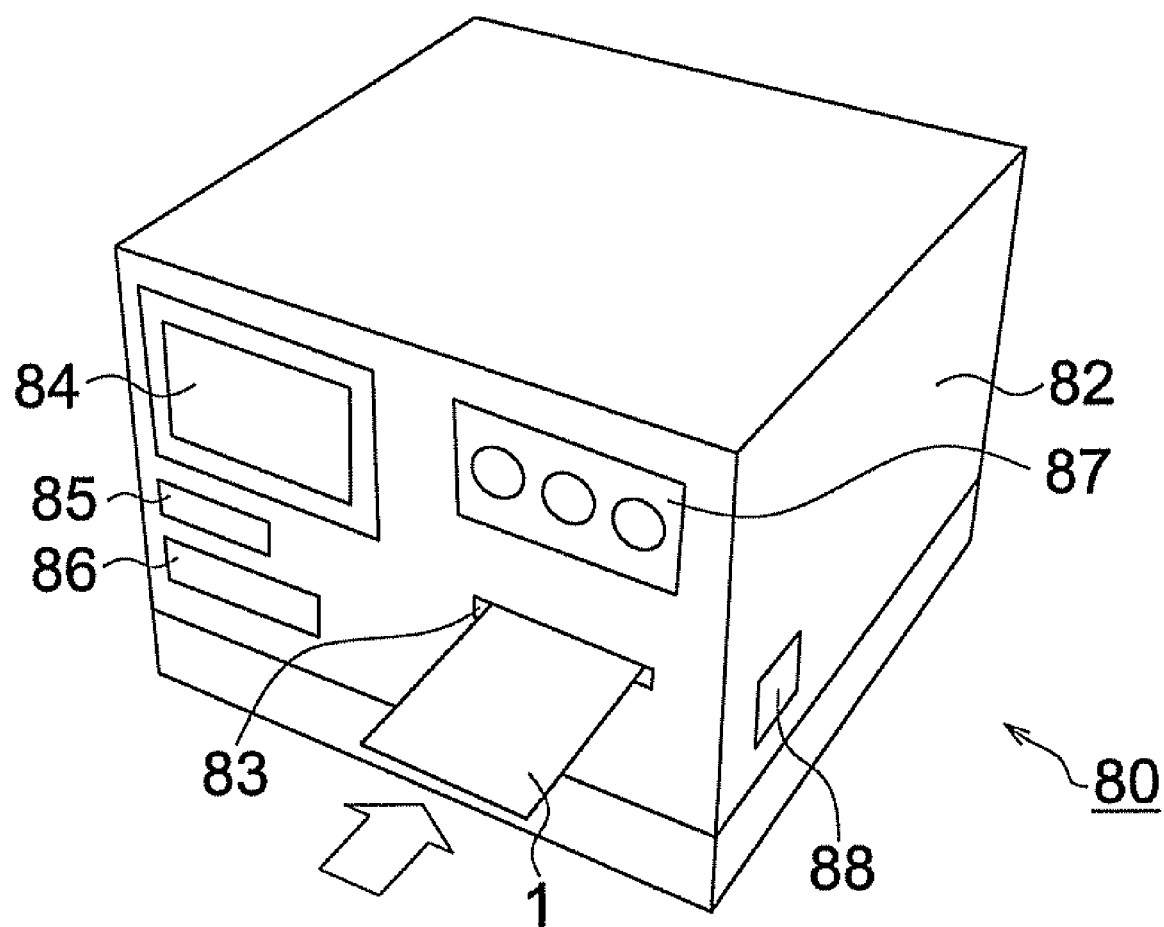
FIG. 1 shows an outer appearance of a microchip inspection system embodied in the present invention.

Referring to the drawings, an embodiment of the present invention will be detailed in the following.

FIG. 1 shows an outer appearance of a microchip inspection system 80 embodied in the present invention.

The microchip inspection system 80 embodied in the present invention is constituted by a reaction detecting apparatus 82 and a microchip 1. The reaction detecting apparatus 82 automatically detects a reaction occurring between a specimen and a reagent, both injected in advance into the microchip 1, so as to display result of the reaction onto a display section 84. The reaction detecting apparatus 82 is provided with a insertion opening 83, so as to make it possible to insert the microchip 1 into the insertion opening 83 and to set the microchip 1 inside the reaction detecting apparatus 82.

In this connection, the height of the insertion opening 83 is set at a value sufficiently greater than the thickness of the microchip 1, so that the microchip 1 does not contact edges of the insertion opening 83 when inserting it. Numeral 85 indicates a memory card slot, numeral 86 indicates a print output opening, numeral 87 indicates an operating panel and numeral 88 indicates an input/output terminal.

The inspection operator inserts the microchip 1 into the insertion opening 83 in a direction indicated by the arrow shown in FIG. 1, and operates the operating panel 87 to commence the inspection. In the reaction detecting apparatus 82, a micro pump unit 5 (not shown in FIG. 1) injects a liquid, such as a driving liquid, etc., into the microchip 1 in response to a command signal sent from a controlling section, so as to automatically implement the inspection of the reaction occurring in the microchip 1. When the inspection is completed, the result of the inspection is displayed on the display section 84 constituted by the LCD (Liquid Crystal Display) panel, etc. Further, the result of the inspection can be outputted as a printout from the print output opening 86, and/or can be stored in a memory card inserted into the memory card slot 85. Still further, it is also possible to store data of the inspection result into a personal computer coupled to the input/output terminal 88 by employing, for instance, a LAN (Local Area Network) cable.

The inspection operator takes out the microchip 1 from the insertion opening 83 after the inspection is finalized.

Next, referring to FIG. 2, an example of the micro pump unit 5 embodied in the present invention will be detailed in the following.

Figure 2:
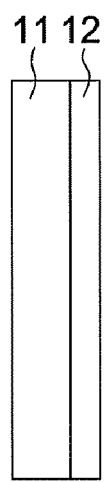
FIG. 2(a) shows a plane view of a micro pump unit embodied in the present invention.
FIG. 2(b) shows a left side view of the same.
FIG. 2(c) shows a right side view of the same and FIG. 2(d) shows a cross sectional view of a portion indicated by the line A-A shown in FIG. 2(a)
Figure 2:
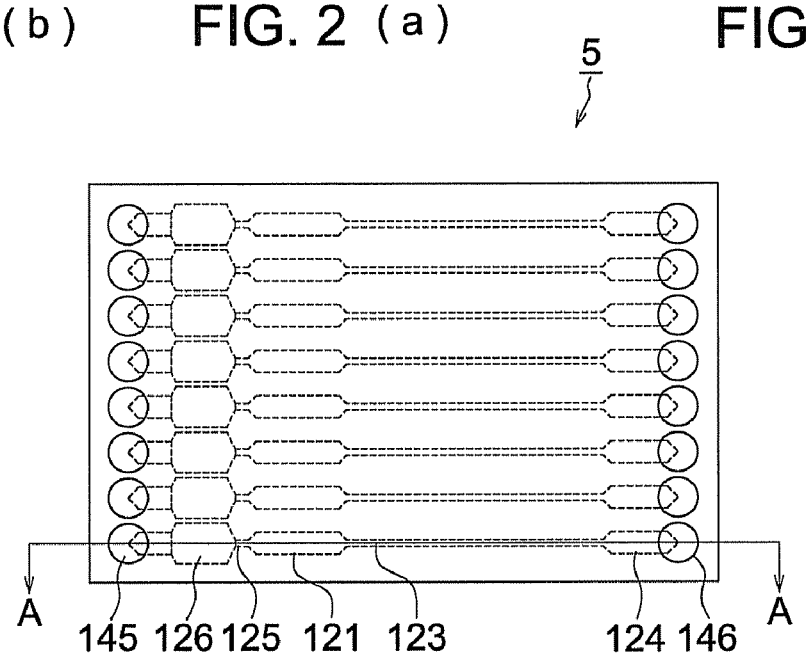
Figure 2:
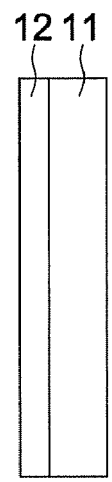
Figure 2:
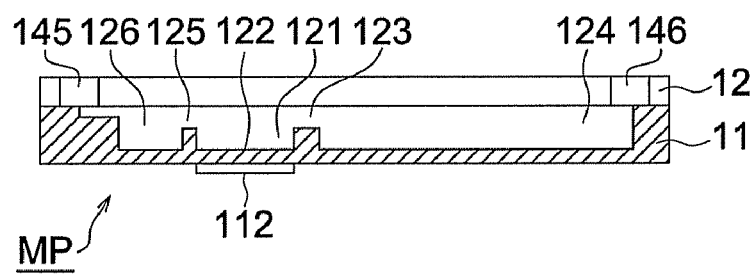

FIG. 2(*a*) shows a plane view of the micro pump unit 5 embodied in the present invention, FIG. 2(*b*) shows a left side view of the same and FIG. 2(*c*) shows a right side view of the same. Further, FIG. 2(*d*) shows a cross sectional view of a portion indicated by the line A-A shown in FIG. 2(*a*).

As shown in FIG. 2(*a*) through FIG. 2(*d*), the micro pump unit 5 is constituted by a first substrate 11 and a second substrate 12. In this connection, in FIG. 2(*a*), groove portions formed on the first substrate 11 are indicated by the dotted lines.

The portion indicated by the line A-A shown in FIG. 2(*a*) structures a micro pump MP in which the liquid absorbed from an intake/outlet opening 145 is emitted from an intake/outlet opening 146 by a micro pump mechanism detailed later. Alternatively, it is also possible to emit the liquid, absorbed from the intake/outlet opening 146, from the intake/outlet opening 145 in the reverse direction of the above. In the example shown in FIG. 2(*a*), eight micro pumps MP are fabricated on the first substrate 11. Since these eight micro pumps MP have the same structure, only referring to FIG. 2(*d*), its structure will be detailed in the following.

The first substrate 11 is shaped in a rectangular sheet having dimensions of, for instance, width: 17 mm, depth: 35 mm and thickness: 0.2 mm. As shown in FIG. 2(*d*), each of the micro pumps MP fabricated on the first substrate 11 is provided with a pump chamber 121, a diaphragm 122, a first narrowed flow path 123, a first liquid flow path 124, a second narrowed flow path 125 and a second liquid flow path 126.

For instance, the first substrate 11 is manufactured by forming a silicon-wafer into a predetermined shape through the well-known photolithography process. Concretely speaking, a patterning processed silicon substrate is etched to a predetermined depth by employing the ICP dry etching apparatus.

After the etching process has completed, the silicon-wafer is cut into a predetermined outer shape by applying the dicing process. The thickness of the first substrate 11 is set at, for instance, around 0.2 mm.

As shown in FIG. 2(*d*), a piezoelectric element 112 is adhered onto the outer surface of the diaphragm 122. The two electrodes for driving the piezoelectric element 112 is led out to both side areas on the face surface of the piezoelectric element 112, so as to connect them to a flexible wire (not shown in the drawings).

The second substrate 12 should tightly adhere onto the first substrate 11 so as to seal the liquid flow path of each of the micro pumps MP, etc., formed on the first substrate 11. For this purpose, it is desirable that the coefficient of thermal expansion of the second substrate 12 is approximated to that of the first substrate 11 as near as possible. When the first substrate 11 is made of silicon, for instance, a Pyrex Glass (Registered Trade Mark of Corning Glass Works Co.), a Tempax Glass (Registered Trade Mark of Schott Glasswork Co.), etc. can be employed as the material of the second substrate 12, since the coefficient of thermal expansions of them are substantially the same as that of the silicon substrate. The dimensions of the second substrate 12 are, for instance, width: 17 mm, depth: 35 mm, which are same as those of the first substrate 11, and thickness: 1 mm.

Next, by employing a method of an ultrasonic machining, etc., perforation machining is applied to the second substrate 12 so as to form the intake/outlet opening 145 and the intake/outlet opening 146. After the perforation machining is completed, the position of the second substrate 12 is adjusted so that two side edge portions of the first substrate 11 and the second substrate 12 coincide with each other, and then, both of them are jointed with each other by employing, for instance, the anode joining treatment.

According to the processes mentioned in the above, it is possible to manufacture the micro pump unit 5. The micro pump unit 5 absorbs the liquid from the intake/outlet opening 145 located one side, while emits the liquid from the intake/outlet opening 146 located the other side, by operating the micro pump MP aforementioned. Further, by controlling the driving voltage to be applied to the piezoelectric element 112, it is possible to reverse the directions of absorbing and emitting. In this connection, with respect to the structure of the first substrate 11 itself, it is possible to refer to Tokkai 2001-322099 (Japanese Non-Examined Patent Publication) as described in the "BACKGROUND OF THE INVENTION".

Next, the operating principle of the micro pump unit 5 will be detailed in the following.

Although the liquid flow path resistance of the second narrowed flow path 125 is relatively low when the differential pressure between the liquid pressures of its liquid intake side and its liquid emission side, the liquid flow path resistance increases with the increase of the differential pressure. In other words, the pressure dependency of the liquid flow path resistance is great. On the other hand, although the liquid flow path resistance of the first narrowed flow path 123 is greater than that of the second narrowed flow path 125 when the differential pressure is approximately zero, the first narrowed flow path 123 has a little pressure dependency of the liquid flow path resistance. Therefore, even if the differential pressure becomes great, the liquid flow path resistance changes a little, and accordingly, the liquid flow path resistance of the first narrowed flow path 123 is smaller than that of the second narrowed flow path 125 when the differential pressure is great.

The abovementioned characteristic of the liquid flow path resistance can be obtained by making the liquid (fluid), flown in the liquid flow path, to be a turburent flow corresponding to an amplitude of the differential pressure, or a laminar (streamline) flow irrespective of an amplitude of the differential pressure. Concretely speaking, for instance, the abovementioned characteristic of the liquid flow path resistance can be realized by making the second narrowed flow path 125 to be an orifice having a short liquid flow path, while by making the first narrowed flow path 123 to be a nozzle having a long liquid flow path and having an inner diameter same as that of the second narrowed flow path 125.

By employing such the characteristic of the liquid flow path resistance of the first narrowed flow path 123 and the second narrowed flow path 125 to generate a pressure in the pump chamber 121, and by controlling the rate of its pressure change, it is possible to generate pumping actions for emitting the liquid toward a lower direction of the liquid flow path resistance.

Concretely speaking, by increasing the pressure of the pump chamber 121 and setting the rate of its pressure change at a high rate, the liquid flow path resistance of the second narrowed flow path 125 becomes greater that that of the first narrowed flow path 123 due to the increase of the differential pressure, and therefore, the liquid residing in the pump chamber 121 is emitted from the first narrowed flow path 123 (emitting process). Successively, by decreasing the pressure of the pump chamber 121 and decreasing the rate of its pressure change, the liquid flow path resistance of the second narrowed flow path 123 becomes greater that that of the first narrowed flow path 125 since the differential pressure is maintained within a range of low value, and therefore, the liquid flows into the pump chamber 121 from the second narrowed flow path 125 (absorbing process).

Conversely, by increasing the pressure of the pump chamber 121 and decreasing the rate of its pressure change, the liquid flow path resistance of the second narrowed flow path 123 becomes greater that that of the first narrowed flow path 125 since the differential pressure is maintained within a range of low value, and therefore, the liquid residing in the pump chamber 121 is emitted from the first narrowed flow path 125 (emitting process). Successively, by decreasing the pressure of the pump chamber 121 and increasing the rate of its pressure change, the liquid flow path resistance of the second narrowed flow path 123 becomes smaller that that of the first narrowed flow path 125 due to the increase of the differential pressure, and therefore, the liquid flows into the pump chamber 121 from the first narrowed flow path 123 (absorbing process).

Such the pressure controlling operation as mentioned in the above can be achieved by controlling the driving voltage to be applied to the piezoelectric element 112 and by controlling the deformation amount of the diaphragm 122 and its timing.

FIG. 3($a$-1), FIG. 3($a$-2), FIG. 3($b$-1) and FIG. 3($b$-2) show explanatory graphs for explaining relationships between a driving voltage E to be applied to the piezoelectric element 112 and a liquid flow amount Q. Hereinafter, it is established that the pressure of the pump chamber 121 increases according as the driving voltage E increases.

Since the relationship of T1<T3 is established in the waveform shown in FIG. 3($a$-1), the change rate at the time when the pressure of the pump chamber 121 increases is greater than that when the pressure of the pump chamber 121 decreases. Accordingly, as aforementioned, the liquid is emitted from the first narrowed flow path 123.

FIG. 3($a$-2) shows an example of the transition of the liquid flow amount Q of the liquid, emitted from the first narrowed flow path 123, at the first liquid flow path 124. During the time interval T1, since the pressure of the pump chamber 121 abruptly increases, the liquid flow amount Q of the liquid, flowing through the first liquid flow path 124, also abruptly increases. During the time interval T3 after the deactivating time interval T2 has elapsed, according as the pressure of the pump chamber 121 gradually decreases, the liquid flows into the pump chamber 121 mainly from the second narrowed flow path 125, and a part of the liquid flows into the pump chamber 121 from the first narrowed flow path 123. Accordingly, the liquid flow amount Q gradually decreases. However, since the liquid flow amount Q, decreasing during the time interval T3, is smaller than that flowing into during the time interval T1, the liquid flow amount Q has increased during the deactivating time interval T4, compared to that of the initial state. By repeating the operation cycle from T1 to T4 in the abovementioned manner, the liquid flow amount Q is gradually increased.

On the other hand, since the relationship of T7<T5 is established in the waveform shown in FIG. 3($b$-1), the change rate at the time when the pressure of the pump chamber 121 increases is smaller than that when the pressure of the pump chamber 121 decreases. Accordingly, as aforementioned, the liquid is flows into the pump chamber 121 from the first narrowed flow path 123.

FIG. 3($b$-2) shows an example of the transition of the liquid flow amount Q of the liquid, absorbed from the first narrowed flow path 123, at the first liquid flow path 124. During the time interval T5, according as the pressure of the pump chamber 121 gradually increases, the liquid is emitted mainly from the second narrowed flow path 125, and a part of the liquid is emitted from the first narrowed flow path 123. Accordingly, the liquid flow amount Q gradually increases. On the other hand, during the time interval T7 after the deactivating time interval T6 has elapsed, since the pressure of the pump chamber 121 abruptly decreases, the liquid flows into the pump chamber 121 from the first narrowed flow path 123. Accordingly, the liquid flow amount Q abruptly decreases. However, since the liquid flow amount Q, increasing during the time interval T5, is smaller than that emitted during the time interval T7, the liquid flow amount Q has decreased during the deactivating time interval T8, compared to that of the initial state. By repeating the operation cycle from T5 to T8 in the abovementioned manner, the liquid flow amount Q is gradually decreased.

In FIG. 3($a$-1) and FIG. 3($b$-1), the maximum voltage e1 to be applied to the piezoelectric element 112 is normally set at a value in a range of several volts to several tens volts, or several hundreds volts at most. Further, each of the time intervals T1 and T7 is set at around 20 μs, each of the time intervals T2 and T6 is set at a value in a range of 0-several μs, and each of the time intervals T3 and T5 is set at around 60 μs. Further, it is also applicable that each of the time intervals T4 and T8 is set at zero μs. Still further, the frequency of the driving voltage E is set at around 11 kHz. By employing the driving voltage E shown in FIG. 3($a$-1) and FIG. 3($b$-1), for instance, the liquid flow amount shown in FIG. 3($a$-2) and FIG. 3($b$-2) can be obtained. In this connection, FIG. 3($a$-2) and FIG. 3($b$-2) schematically show the characteristic curves of the liquid flow amount obtained by the pumping actions. In reality, the other curves of the fluid inertia vibrations are superimposed onto the characteristic curves shown in FIG. 3($a$-2) and FIG. 3($b$-2). Accordingly, the curves derived by superimposing the vibration components onto the characteristic curves shown in FIG. 3($a$-2) and FIG. 3($b$-2) indicate the correct curves indicating liquid flow amounts to be really obtained.

Next, referring to FIG. 4($a$), FIG. 4($b$) and FIG. 4($c$), an example of the microchip 1 embodied in the present invention will be detailed in the following.

Figure 4:
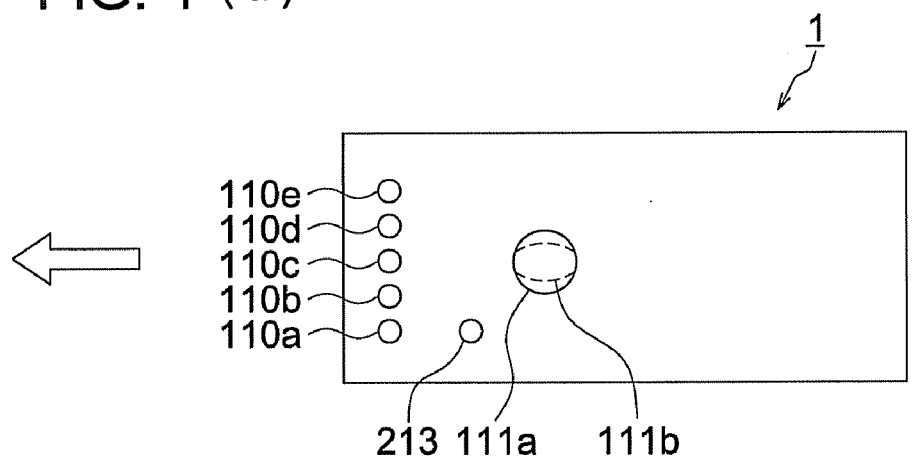
FIG. 4(a) shows an upper surface of a microchip when inserting it into a reaction detecting apparatus.
FIG. 4(b) shows a side view of a microchip.
FIG. 4(c) shows a explanatory drawing for explaining functions of fine liquid flow paths and liquid flow path elements disposed in a microchip.
Figure 4:
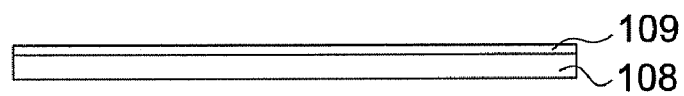
Figure 4:
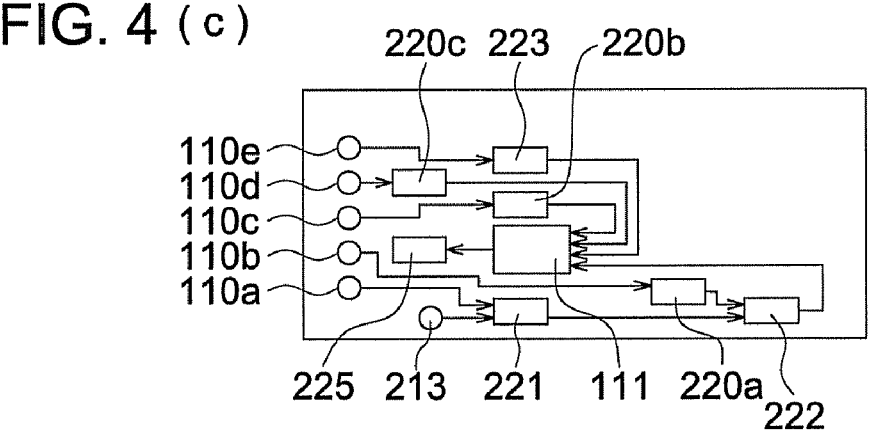

FIG. 4($a$) and FIG. 4($b$) show outer appearances of the microchip 1. The arrow shown in FIG. 4($a$) indicates an inserting direction in which the microchip 1 is inserted into the reaction detecting apparatus 82 detailed later. FIG. 4($a$) shows an upper surface of the microchip 1 when inserting it into the reaction detecting apparatus 82, while FIG. 4($b$) shows a side view of the microchip 1.

A detecting window 111*a* and a liquid flow path 111*b* located at the detecting section, shown in FIG. 4($a$), are made of a transparent material such as a glass, a resin, etc., so as to make it possible to optically detect the reaction between the specimen and the reagent. Numerals 110*a*, 110*b*, 110*c*, 110*d* and 110*e* indicate driving liquid injecting sections coupled through the fine liquid flow path disposed inside the microchip 1, from each of which the driving liquid is injected so as to drive the reagent, etc. residing inside. Numeral 213 indicates a specimen injecting section to inject the specimen into the microchip 1.

As shown in FIG. 4($b$), the microchip 1 is constituted by a groove formed substrate 108 and a covering substrate 109 to cover the groove formed substrate 108. Next, the material to be employing for the groove formed substrate 108 and the covering substrate 109, constituting the microchip 1, will be detailed in the following.

It is desirable that It has been desired that the material to be employed for the microchip 1 has good character in workability, anti-water absorbing property, chemical resistance property, heat resistance property and inexpensiveness. Accordingly, considering a structure, a use, a detecting method of the microchip 1, the material of the microchip 1 is selected. Various kinds of materials well-known in the market can be employed as the material of the microchip 1, and the substrate and the liquid flow path elements are formed by combining one or more number of materials corresponding to each of the material characteristics.

Specifically, it is desirable that the microchip for handling a large number of specimens, among other things clinical specimens having risks of contamination and contagious properties, is a disposable type. For this purpose, plastic resins, which are suitable for mass production, and are light in weight, robust against impact, and are easy to be disposed by incineration, for instance, such as polystyrene, can be preferably employed. Further, in such a case that it is needed to be heated up to around 100° C., the resin superior in heat resistance (for instance, such as a polycarbonate, etc.) is preferable employed. Still further, in such a case that the adsorption of protein is a problem, it is preferable to employ a polypropylene. Since the thermal conductivity of a resin, a glass, or the like is relatively small, by using such the material for the locally heated area of the microchip, it becomes possible to selectively heat the heating area only, since the thermal conductivity in the surface direction is suppressed.

When optically detecting a substance created by the color reaction, a fluorescent material, etc. in a detecting section 111, a material having a light transmissible property (for instance, an alkali glass, a quartz glass, transparent plastic materials) should be employed for at least a substrate of this sectional area, so that the light can pass through the substrate. In the present embodiment, a material having a light transmissible property is employed for the detecting window 111a and at least the groove formed substrate 108, which forms the liquid flow path 111b, so that the light can pass through the detecting section 111.

In the microchip 1 embodied in the present invention, microscopic liquid flow paths shaped in grooves (fine liquid flow paths) and functional parts (liquid flow path elements) are disposed in an appropriate manner corresponding to usages of them. In the present embodiment, an example of the amplification of a specific gene to be conducted by the fine liquid flow paths and the liquid flow path elements within the microchip 1 and an exemplified processing for detecting it, will be detailed in the following, referring to FIG. 4(c). Incidentally, the application of the present invention is not limited to the example described referring to FIG. 4(c), but the present invention can be applied to the microchip 1 for various kinds of usages.

FIG. 4(c) shows a explanatory drawing for explaining the functions of the fine liquid flow paths and the liquid flow path elements disposed in the microchip 1.

For instance, a specimen reservoir 221 to accommodate a specimen liquid, a reagent reservoir 220 to accommodate a reagent, etc., are formed in the fine liquid flow paths. Further, a processing liquid necessary for the inspection, such as a kind of reagent, a detergent liquid, a degeneration processing liquid, etc., is accommodated in advance in the reagent reservoir 220, so that the inspection can be performed speedily irrespective of the place or the time. In FIG. 4(c), the liquid flow path elements are indicated by the rectangular blocks, and the fine liquid flow paths coupling them with each other are indicated by the solid lines with arrows.

The microchip 1 is constituted by the groove formed substrate 108, on which the fine liquid flow paths are formed, and the covering substrate 109, which covers the groove-shaped liquid flow paths. The fine liquid flow paths are formed in order of micrometers, and for instance, the dimension of its width is set at a value in a range of several μm-several hundreds μm, preferably in a range of 10-200 μm, while the dimension of its depth is set at a value in a range of around 25 μm-500 μm, preferably in a range of 25-250 μm.

The fine liquid flow paths mentioned in the above are formed on the groove formed substrate 108 of the microchip 1. Further, the covering substrate 109 should cover the groove formed substrate 108 so as to tightly seal the fine liquid flow paths, and may cover all over the groove formed substrate 108. In this connection, for instance, the sections for controlling the liquid conveying operation (not shown in the drawings), such as a liquid conveyance controlling section, a backward flow preventing section (including a check valve, an active valve, etc.), etc., are equipped in the fine liquid flow paths of the microchip 1, so as to prevent the backward flow and to conduct the liquid conveying operations according to a predetermined procedure.

The specimen injecting section 213 is an injecting section to inject the specimen into the microchip 1, while the driving liquid injecting section 110 is another injecting section to inject the driving liquid into the microchip 1. Preceding to implementation of the inspection using the microchip 1, the inspector injects the specimen from the specimen injecting section 213 into the microchip 1 by using a syringe or the like. As shown in FIG. 4(c), the specimen injected from the specimen injecting section 213 is conveyed through the fine liquid flow path coupled to the specimen reservoir 221, and then, accommodated in the specimen reservoir 221.

Successively, injecting the driving liquid from the driving liquid injecting section 110a, the driving liquid passes through the fine liquid flow path coupled to the specimen reservoir 221, and pushes out the specimen accommodated in the specimen reservoir 221, so as to convey the specimen into an amplifying section 222.

On the other hand, the driving liquid injected from the driving liquid injecting section 110b passes through the fine liquid flow path coupled to a reagent reservoir 220a, and pushes out a reagent "a" accommodated in the reagent reservoir 220a. Then, the reagent "a" pushed out from the reagent reservoir 220a is also conveyed into the amplifying section 222 by the driving liquid. Depending on the reacting condition at this time, it is necessary to set the temperature of the amplifying section 222 at a predetermined temperature. For this purpose, a heating operation or a heat absorbing operation is conducted inside the reaction detecting apparatus 82, so as to implement the reaction at the predetermined temperature, as detailed later.

After a predetermined reaction time interval has elapsed, the solution, including the reacted specimen and conveyed out from the amplifying section 222 by the driving liquid, is injected into the detecting section 111. The injected solution reacts to a reaction substance born by the wall of the liquid flow path of the detecting section 111, so as to solidify the solution and to stick the solidified solution onto the wall.

Still successively, injecting the driving liquid from the driving liquid injecting section 110c, the driving liquid passes through the fine liquid flow path coupled to a reagent reservoir 220b, and pushes out the reagent "b" accommodated in the reagent reservoir 220b, so as to convey the reagent "b" into the detecting section 111.

As well as the above, injecting the driving liquid from the driving liquid injecting section 110d, the driving liquid passes through the fine liquid flow path coupled to a reagent reservoir 220c, and pushes out the reagent "c" accommodated in the reagent reservoir 220c, so as to convey the reagent "c" into the detecting section 111.

Finally, the driving liquid is injected from the driving liquid injecting section 110e to push out the detergent liquid accommodated in a detergent liquid reservoir 223, in order to inject the detergent liquid into the detecting section 111. Then, a non-reacted solution 41 remaining in the detecting section 111 is deterged by the detergent liquid.

After the deterging operation is completed, a target detecting object, such as the amplified gene, etc., is detected by optically measuring the density of the reacted substance adhered onto the wall of the liquid flow path of the detecting section 111. As described in the foregoing, by sequentially injecting the driving liquid from the driving liquid injecting section 110, the predetermined processing can be achieved in the microchip 1.

Figure 5:
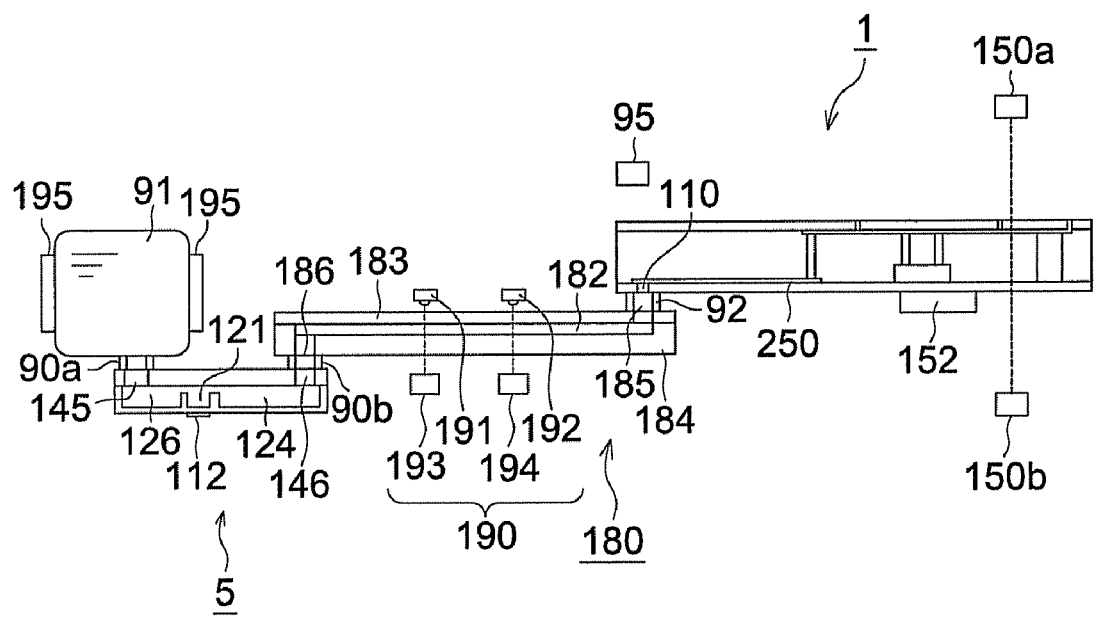
FIG. 5 shows a cross sectional schematic diagram of an internal configuration of a reaction detecting apparatus in a microchip inspection system embodied in the present invention as the first embodiment.

FIG. 5 shows a cross sectional schematic diagram of an internal configuration of the reaction detecting apparatus 82 in the microchip inspection system 80 embodied in the present invention as the first embodiment. The reaction detecting apparatus 82 is constituted by a temperature controlling unit 152, an optical detecting section 150, an intermediate liquid flow path section 180, the micro pump unit 5, packing 90a, 90b, a driving liquid tank 91, a liquid temperature adjusting unit 195, etc. In the following, the number same as that of the element previously explained is attached to an element same as the element previously explained, and the explanation of that will be omitted.

FIG. 5 indicates such a state that the temperature controlling unit 152 and the micro pump unit 5 are tightly fixed onto the upper surface of the microchip 1. The microchip 1 is driven by a driving member (not shown in the drawings), so as to make it movable in the upper-lower direction of the drawing.

In the initial state, the microchip 1 is detachable in the left-right direction of the drawing. The inspector inserts the microchip 1 from the insertion opening 83 until the microchip 1 contacts a regulating member (stopper member, not shown in the drawings). When the microchip 1 is inserted to a predetermined position and a chip detecting section 95, employing a photo-interrupter, etc., detects the microchip 1, the chip detecting section 95 turns ON.

The temperature controlling unit 152 incorporates a Peltier element, a power source, a temperature controlling device, etc., to adjust the temperature of the lower surface of the microchip 1 at a predetermined temperature by conducting a heating operation or a heat absorbing operation.

When a control section (not shown in the drawings) receives a signal indicating that the chip detecting section 95 turns ON, the control section activates the driving member to make the microchip 1 descend, so that the lower surface of the microchip 1 is pushed against the temperature controlling unit 152 and the intermediate liquid flow path section 180 through a packing 92 to make them tightly fixed to each other.

The driving liquid injecting section 110 of the microchip 1 is disposed at such a position that a corresponding opening 185, equipped at the intermediate liquid flow path section 180, and the driving liquid injecting section 110 are coupled trough relative to each other, when making them to be tightly fixed to each other. The intermediate liquid flow path section 180 is constituted by a first transparent substrate 184 having a groove of an intermediate liquid flow path 182 and a second transparent substrate 183 covering the first transparent substrate 184. An opening 186 is coupled to the intake/outlet opening 146 of the micro pump unit 5 through the packing 90b.

The driving liquid tank 91 is coupled to the absorbing side of the micro pump unit 5 through the packing 90a, so that the micro pump unit 5 absorbs the driving liquid filled in the driving liquid tank 91 through the packing 90a. On the other hand, since the intake/outlet opening 146 disposed on an edge surface located at the emitting side of the micro pump unit 5 is coupled to the driving liquid injecting section 110 through the intermediate liquid flow path 182, the driving liquid fed from the micro pump unit 5 is injected into a liquid flow path 250 formed in the microchip 1. As mentioned in the above, the driving liquid is injected into the driving liquid injecting section 110 from the micro pump unit 5.

The liquid temperature adjusting unit 195 incorporates a Peltier element, a power source, a temperature controlling device, etc., to adjust the temperature of the driving liquid tank 91 at a predetermined temperature by conducting a heating operation or a heat absorbing operation. In this connection, although the liquid temperature adjusting unit 195 is attached to the driving liquid tank 91 in such a manner that both of them tightly contact with each other in the present embodiment, the scope of the present invention is not limited to the above. It is also applicable that the liquid temperature adjusting unit 195 is equipped inside of the driving liquid tan 91.

The intermediate liquid flow path section 180 is equipped with a driving liquid detecting device 190 to measure a fluid velocity of the driving liquid currently flowing through the intermediate liquid flow path 182. The driving liquid detecting device 190 is constituted by a first light emitting section 193, a first light receiving section 191, a second light emitting section 194, a second light receiving section 192, a first detecting section 310 (not shown in FIG. 5) and a second detecting section 320 (refer to FIG. 6).

Each of the first light emitting section 193 and the second light emitting section 194 is a light emitting element, such as a LED (Light Emitting Diode), a lamp, etc. Each of the first light receiving section 191 and the second light receiving section 192 is a light receiving element, such as, for instance, a photodiode, etc., to receive the light, emitted from each of the first light emitting section 193 and the second light emitting section 194, which are disposed opposite to the first light receiving section 191 and the second light receiving section 192, respectively, and passing through the intermediate liquid flow path section 180 being transparent. When the driving liquid flows into the intermediate liquid flow path section 180, an amount of light penetrated through the intermediate liquid flow path 182 decreases, and accordingly, the signal electric currents generated by the first light receiving section 191 and the second light receiving section 192 are also decreases.

Each of the first detecting section 310 and the second detecting section 320 is constituted by an amplifier, such as an operational amplifier, etc., a comparator to compare inputted voltage value with a predetermined voltage value, a power source, etc. Each of the first detecting section 310 and the second detecting section 320 converts the signal electric current generated by each of the first light receiving section 191 and the second light receiving section 192 to a corresponding voltage value, and compares the voltage value with the predetermined voltage value, so as to output a detected signal.

As shown in FIG. 5, a pair of the first light emitting section 193 and the first light receiving section 191, and another pair of the second light emitting section 194 and the second light receiving section 192, are disposed at separate positions located within a longitudinal range of the intermediate liquid flow path 182. As detailed later, a fluid velocity calculating section 410 (not shown in FIG. 5, refer to FIG. 6) calculates a fluid velocity of the driving liquid from a time difference between a time when the first detecting section 310 outputs the detecting signal and another time when the second detecting section 320 outputs the detecting signal.

In this connection, although the driving liquid detecting device 190 is equipped to measure the fluid velocity of the driving liquid flowing into the intermediate liquid flow path section 180 in the present embodiment, the position, at which the driving liquid detecting device 190 is to be equipped, is not limited to the intermediate liquid flow path section 180. Further, the intermediate liquid flow path section 180 is not always necessary. For instance, it is also applicable that the driving liquid detecting device 190 is equipped for measuring the fluid velocity of the driving liquid flowing into the first liquid flow path 124 of the micro pump unit 5.

Further, although the driving liquid is detected by receiving the light penetrated through the driving liquid, the scope of the present invention is not limited to the penetrated light. It is also applicable to detect the driving liquid by employing a reflected light.

Still further, although eight micro pumps MP are equipped in the example of the micro pump unit 5 shown in FIG. 2, it is not necessary to use all of the eight micro pumps MP. In the case of the microchip 1 shown in FIG. 3, it is applicable to arrange the driving liquid injecting section 110 so that five micro pumps MP are availably coupled through.

In the detecting section 111 of the microchip 1, for instance, color reaction, light emission, fluorescent light emission, muddiness reaction, etc. would occur as a result of reaction between the specimen and the reagent stored in the microchip 1. In the present embodiment, as explained referring to FIG. 4, the reaction result of the reagent occurring in the detecting section 111 is optically detected. The optical detecting section 150 is equipped with a third light emitting section 150a and a third light receiving section 150b, so as to make it possible to detect the light penetrated through the detecting section 111 of the microchip 1.

Figure 6:
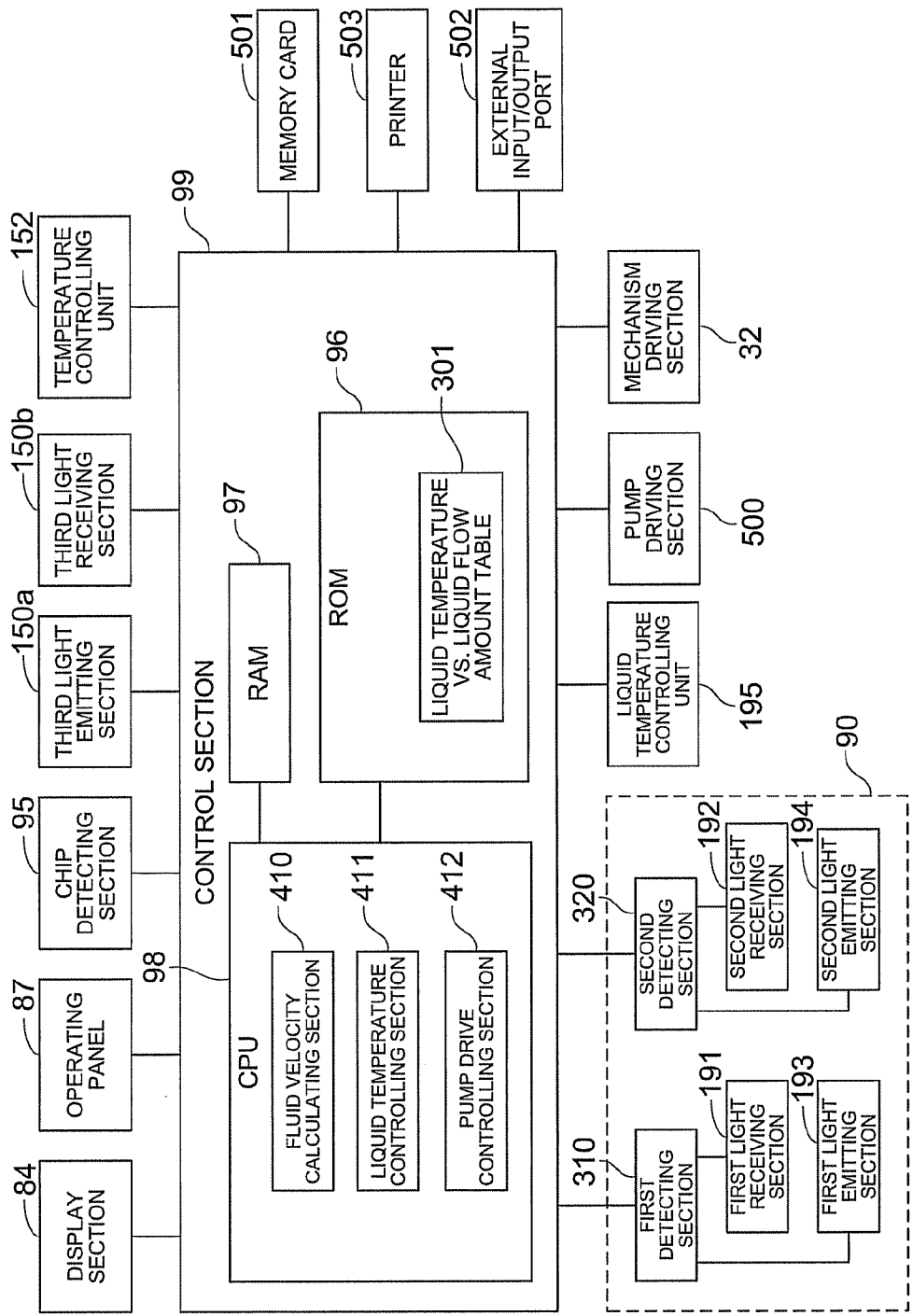
FIG. 6 shows a circuit block diagram of a microchip inspection system embodied in the present invention as the first embodiment.

FIG. 6 shows a circuit block diagram of the microchip inspection system 80 embodied in the present invention as the first embodiment.

A control section 99 is constituted by a CPU (Central Processing Unit) 98, a RAM (Random Access Memory) 97, a ROM (Read Only Memory) 96, etc. The control section 99 reads out programs stored in the ROM 96 serving as a nonvolatile storage section, and conducts concentrate controlling operations for various sections, included in the microchip inspection system 80, according to the programs concerned.

In the following, the same reference number is attached to the functional block having the same function described in the foregoing, and the explanation for it will be omitted.

The chip detecting section 95 transmits the detection signal to the CPU 98 when the microchip 1 contacts the regulating member (stopper). Receiving the detection signal, the CPU 98 sends a command signal to a mechanism driving section 32 to make the microchip 1 descend or ascend according to the predetermined procedures.

A pump driving section 500 serves as a driving section to drive the piezoelectric element 112 of each micro pump MP. A pump drive controlling section 412 controls the pump driving section 500 based on the program concerned, so as to inject or absorb a predetermined amount of the driving liquid. Receiving a command signal sent from the pump drive controlling section 412, the pump driving section 500 generates the driving voltage E having the waveform shown in FIG. 3, to drive the piezoelectric element 112.

The CPU 98 implements the inspection in a predetermined sequence, and stores the inspection result into the RAM 97. By operating an operating panel 87, it is possible not only to store the inspection result into a memory card 501, but also to print the inspection result by employing a printer 503.

The driving liquid detecting device 190 of the present embodiment is constituted by the first light emitting section 193, the first light receiving section 191, the second light emitting section 194, the second light receiving section 192, the first detecting section 310 and the second detecting section 320. In response to the command signal sent from the CPU 98, the first light emitting section 193 and the second light emitting section 194 emits light. Each of the first detecting section 310 and the second detecting section 320 detects a change of the light amount caused by a passage of the driving liquid, and generates the detection signal, which is to be inputted into the CPU 98. A fluid velocity calculating section 410 calculates a fluid velocity V of the driving liquid from a time difference "t" of the detection signals inputted from the first light receiving section 191 and the second light receiving section 192. The fluid velocity calculating section 410 serves as a fluid velocity calculating section of the present invention.

The fluid velocity V can be found by employing Eq. (1) indicated as follow. Further, a cross sectional area S of the intermediate liquid flow path 182 is kept constant.

$$V = x/t \qquad \text{Eq. (1)}$$

where x: distance between first light receiving section 191 and second light receiving section 192.

Further, since the cross sectional area S of the intermediate liquid flow path 182 is kept constant, the liquid flow amount Q can be found by employing Eq. (2) indicated as follow.

$$Q = V \times S \qquad \text{Eq. (2)}$$

After the liquid flow amount Q has been found, a liquid temperature controlling section 411 finds a target liquid temperature by referring to a liquid temperature vs. liquid flow amount table 301, and sends a command signal to the liquid temperature adjusting unit 195. The liquid temperature controlling section 411 serves as a liquid temperature controlling section of the present invention, and the liquid temperature adjusting unit 195 serves as a liquid temperature controlling unit of the present invention.

Figure 7:
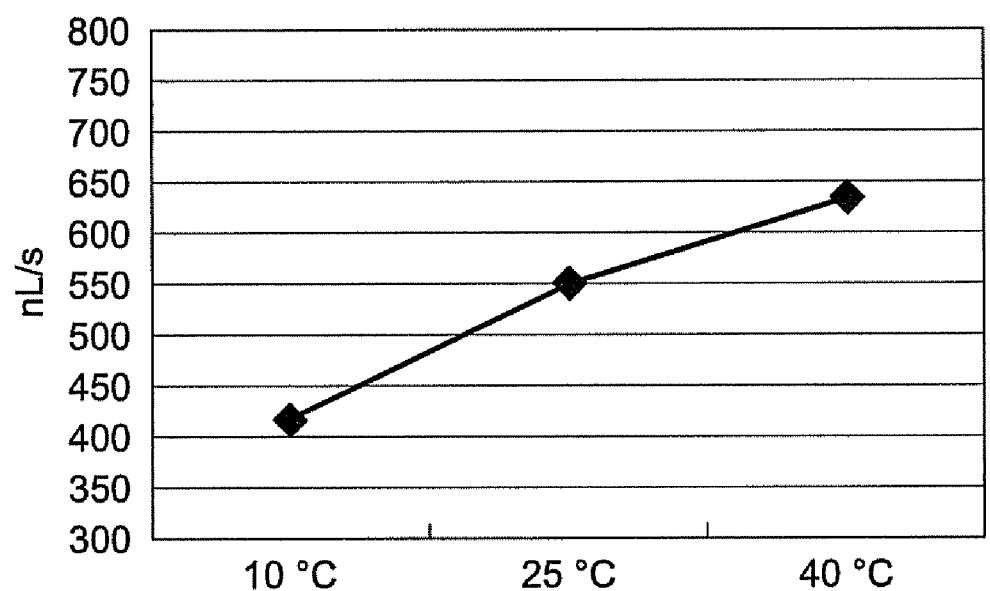
FIG. 7 shows a graph indicating an exemplary relationship between a liquid temperature and a liquid flow amount.

FIG. 7 shows a graph indicating an exemplary relationship between the liquid temperature and the liquid flow amount.

Concretely speaking, the graph shown in FIG. 7 indicates a measuring result of the liquid flow amount in the intermediate liquid flow path 182, which is acquired by driving the micro pump MP under the same condition, while setting the liquid temperature as the parameter. In FIG. 7, the horizontal axis represents the liquid temperature (° C.), while the vertical axis represents the liquid flow amount Q (nl/sec.). As shown in FIG. 7, according as the liquid temperature increases, the liquid flow amount Q increases, since the viscosity of the driving liquid decreases. The liquid temperature vs. liquid flow amount table 301 is derived from the relationship between the liquid temperature and the liquid flow amount indicated by the graph shown in FIG. 7.

Figure 8:
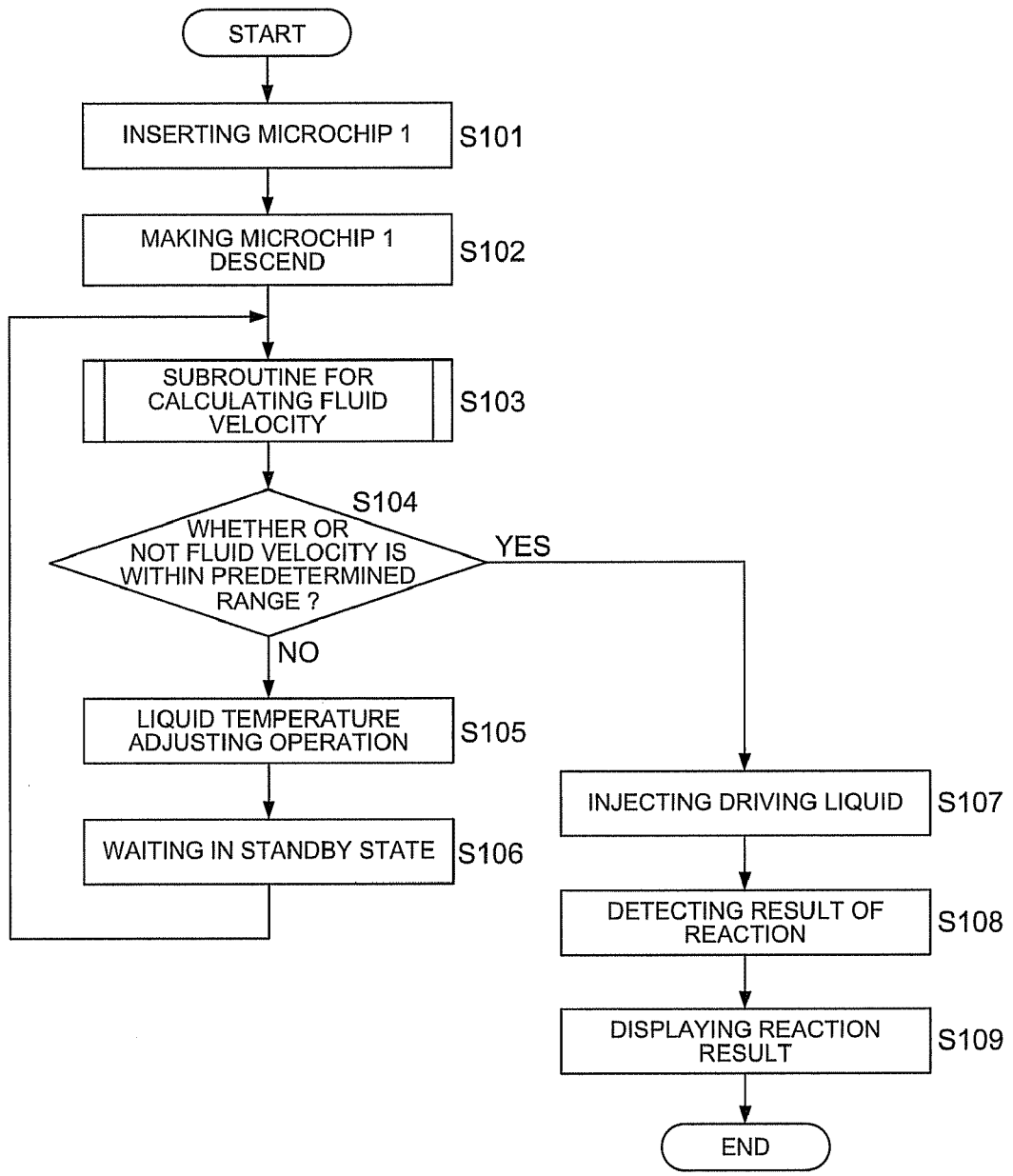
FIG. 8 shows a flowchart for explaining an inspection procedure to be conducted in a microchip inspection system embodied in the present invention.

FIG. 8 shows a flowchart for explaining the inspection procedure to be conducted in the microchip inspection system 80 embodied in the present invention.

In the flowchart shown in FIG. 8, it is assumed that the temperature controlling unit 152 is activated at the time when the reaction detecting apparatus 82 is turned ON, and is kept at a predetermined temperature.

Step S101: inserting the microchip 1 from the insertion opening 83.

The inspector inserts the microchip 1 from the insertion opening 83 until it contacts the regulating member (stopper, not shown in the drawings)

Step S102: making the microchip 1 descend by controlling the mechanism driving section 32.

When the microchip 1, inserted from the insertion opening 83, contacts the regulating member (stopper, not shown in the drawings) and the CPU 98 receives the detection signal sent from the chip detecting section 95, the CPU 98 controls the mechanism driving section 32, so as to make the microchip 1 descend until the microchip 1 tightly contacts the packing 92 and the temperature controlling unit 152 with an appropriate pressure.

Step S103: calculating the fluid velocity.

The CPU 98 calls a fluid velocity measuring subroutine to calculate the fluid velocity of the driving liquid currently flowing in the intermediate liquid flow path 182.

Step S104: determining whether or not the fluid velocity measured in Step S103 is a value within a predetermined range.

Although the predetermined fluid velocity varies depending on the specification of the micro pump MP, it is acceptable that the fluid velocity is in a range of, for instance, ±10% of the predetermined fluid velocity.

When the fluid velocity is not a value within a predetermined range (Step S104; No), the inspection procedure proceeds to Step S105.

When the fluid velocity is a value within a predetermined range (Step S104; Yes), the inspection procedure proceeds to Step S107.

Step S105: conducting the liquid temperature adjusting operation.

The liquid temperature controlling section 411 finds the liquid flow amount Q from the fluid velocity measured in Step S103, and instructs the target liquid temperature to the liquid temperature adjusting unit 195 by referring to the liquid temperature vs. liquid flow amount table 301.

Step S106: waiting in a standby state.

The liquid temperature controlling section 411 estimates a time interval necessary for setting the liquid temperature at the target liquid temperature, and waits in a standby state until the estimated time interval is elapsed.

After Step S106 is completed, the inspection procedure returns to Step S103, in order to measure the fluid velocity again.

Step S107: injecting the driving liquid into the microchip 1.

According to the predetermined sequence, the pump drive controlling section 412 sends command signals to the pump driving section 500, so as to make the pump driving section 500 drive the micro pumps MP to sequentially inject the driving liquid into the driving liquid injecting section 110 of the microchip 1. The injected driving liquid conveys the specimen and the reagent into the detecting section 111 according to the predetermined sequence, so as to make them react to each other.

Step S108: detecting the result of reaction occurring in the detecting section 111.

After the predetermined reaction time has elapsed, the CPU 98 makes the third light emitting section 150a emit light to illuminate the detecting section 111 of the microchip 1, and then, receives input signals sent from the third light receiving section 150b, which receives a light penetrated through the detecting section 111, so that an analogue-to-digital converter incorporated in the CPU 98 converts the input signals to a digital value, to acquire a photometry value.

Step S109: displaying the reaction result.

The CPU 98 conducts the arithmetic calculation based on the result of the photometry conducted by the optical detecting section 150, and makes the display section 84 display the reaction result.

Then, the inspection procedure is finalized.

Figure 9:
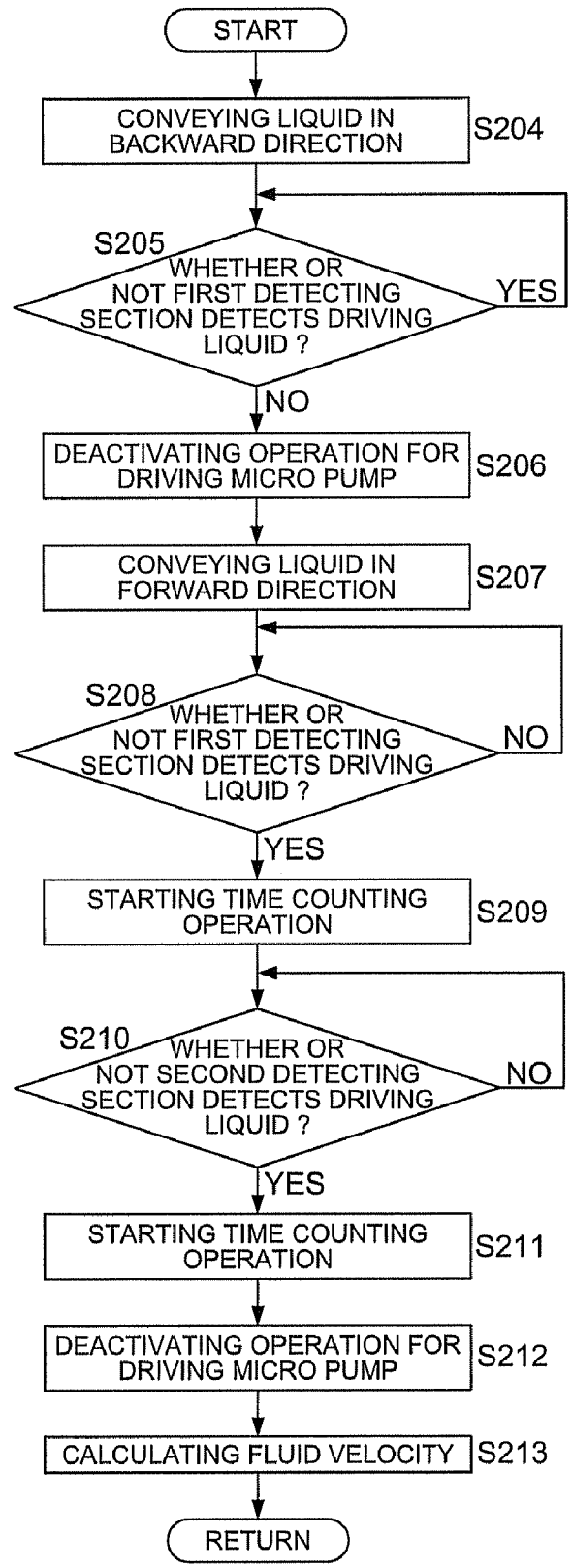
FIG. 9 shows a flowchart of a fluid velocity measuring subroutine.
Figure 10:
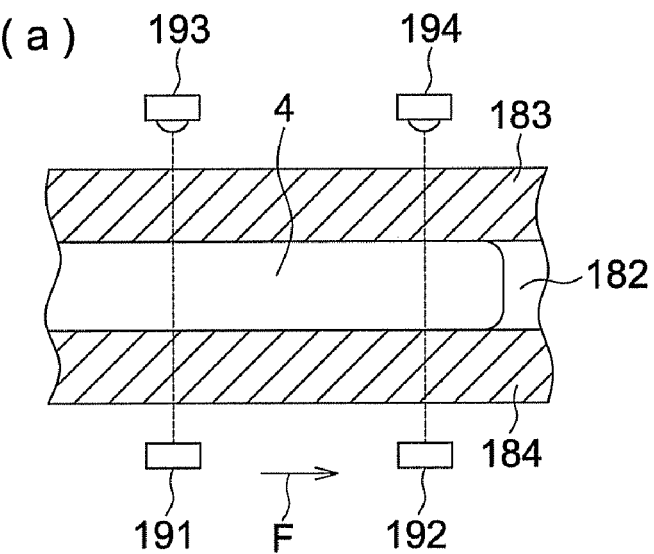
FIG. 10(a), FIG. 10(b) and FIG. 10(c) are enlarged cross sectional views of a portion at which a driving liquid detecting device is equipped in an intermediate liquid flow path section.
Figure 10:
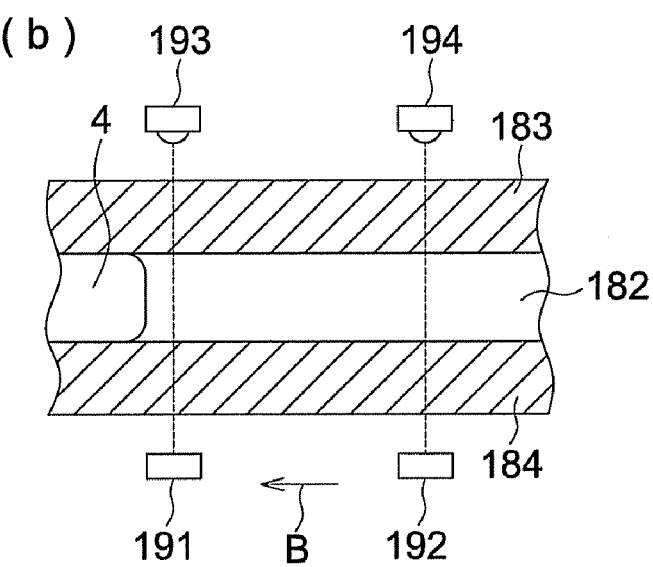
Figure 10:
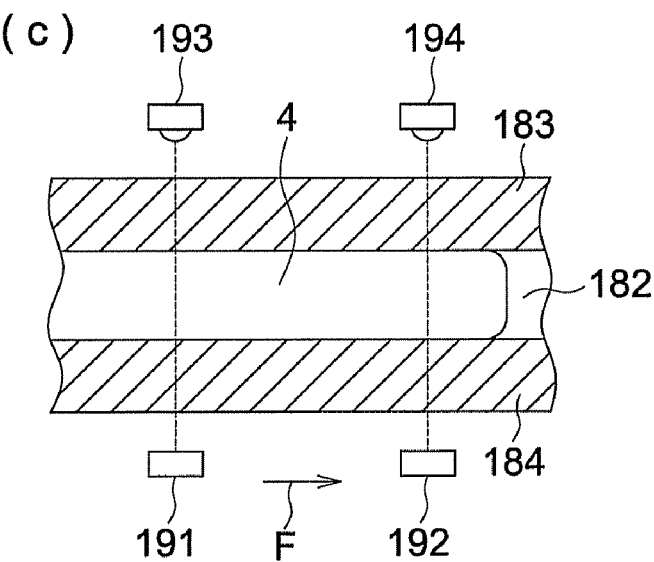

Next, referring to FIG. 9 and FIG. 10, the procedure of the fluid velocity measuring subroutine will be detailed in the following. FIG. 9 shows a flowchart of the fluid velocity measuring subroutine, while FIG. 10(*a*), FIG. 10(*b*) and FIG. 10(*d*) show explanatory drawings for explaining the movements of a driving liquid 4 during the fluid velocity measuring operation. FIG. 10(*a*), FIG. 10(*b*) and FIG. 10(*d*) are enlarged cross sectional views of a portion at which the driving liquid detecting device 190 is equipped in the intermediate liquid flow path section 180, and indicating the leading edge portion of the driving liquid 4 residing in the intermediate liquid flow path 182. Herein, at the initial state, it is assumed that the leading edge portion of the driving liquid 4 is located at the position shown in FIG. 10(*a*).

According to the flowchart shown in FIG. 9, the movements of the driving liquid 4 indicated in FIG. 10(*a*), FIG. 10(*b*) and FIG. 10(*d*) will be detailed in the following.

Step S204: conveying the liquid in a backward direction.

The pump drive controlling section 412 sends a command signal to the pump driving section 500, so that the pump driving section 500 drives the micro pump MP so as to convey the liquid in a backward direction. In this connection, the backward direction is defined as a direction opposite to the direction of injecting the driving liquid 4 into the microchip 1, and indicated by arrow B shown in FIG. 10(*b*).

Step S205: determining whether or not the first detecting section 310 detects the driving liquid.

The fluid velocity calculating section 410 determines whether or not the first detecting section 310 detects the driving liquid, based on the light amount received by the first light receiving section.

When the first detecting section 310 detects the driving liquid (Step S205; Yes), the flowchart returns to Step S205.

When the first detecting section 310 does not detect the driving liquid (Step S205; No), the flowchart proceeds to Step S206. FIG. 10(*b*) shows such a state that the driving liquid 4 is conveyed in the reverse direction, to such a extent that the first detecting section 310 cannot detect the driving liquid 4.

Step S206: deactivating the operation for driving the micro pump MP.

The pump drive controlling section 412 sends a command signal to the pump driving section 500, so that the pump driving section 500 deactivates the operation for driving the micro pump MP, Step S207: conveying the liquid in a forward direction.

The pump drive controlling section 412 sends a command signal to the pump driving section 500, so that the pump driving section 500 drives the micro pump MP so as to convey the liquid in a forward direction. In this connection, the forward direction is defined as a direction of injecting the driving liquid 4 into the microchip 1, and indicated by arrow F shown in FIG. 10(*c*).

Step S208: determining whether or not the first detecting section 310 detects the driving liquid.

The fluid velocity calculating section 410 determines whether or not the first detecting section 310 detects the driving liquid.

When the first detecting section 310 does not detect the driving liquid 4 (Step S208; No), the flowchart returns to Step S208.

When the first detecting section 310 detects the driving liquid 4 (Step S208; Yes), the flowchart proceeds to Step S209.

Step S209: starting an operation for counting the time.

The fluid velocity calculating section 410 initializes an internal counter for measuring the time, and starts the counting operation.

Since the leading edge of the driving liquid 4 passes through the position of the first light receiving section 191, the counting operation to be performed by the internal counter is commenced.

Step S210: determining whether or not the second detecting section 320 detects the driving liquid.

The fluid velocity calculating section 410 determines whether or not the second detecting section 320 detects the driving liquid.

When the second detecting section 320 does not detect the driving liquid 4 (Step S208; No), the flowchart returns to Step S210.

When the second detecting section 320 detects the driving liquid 4 (Step S210; Yes), the flowchart proceeds to Step S211.

In Step S210, the leading edge of the driving liquid 4 passes through the position of the second light receiving section 192, as shown in FIG. 10(c).

Step S211: stopping an operation for counting the time.

The fluid velocity calculating section 410 stops the internal counter for measuring the time.

Since the leading edge of the driving liquid 4 passes through the position of the second light receiving section 192, the counting operation to be performed by the internal counter is halted.

Step S212: deactivating the operation for driving the micro pump MP.

The pump drive controlling section 412 sends a command signal to the pump driving section 500, so that the pump driving section 500 deactivates the operation for driving the micro pump MP.

Step S213: calculating the fluid velocity.

The fluid velocity calculating section 410 calculates the fluid velocity from the value indicated by the internal counter for counting the time.

Then, the subroutine is finalized, and the program returns to the main routine.

As described in the foregoing, before the process of Step S107 in which the micro pump MP injects the driving liquid into the microchip 1, the driving liquid detecting device 190 detects the information that the driving liquid passes through the intermediate liquid flow path 182, serving as a liquid flow path for injecting the driving liquid into the microchip 1 in the process of Step S103. Since the fluid velocity calculating section 410 calculates the fluid velocity and controls the temperature of the driving liquid, based on the abovementioned information, the fluid velocity of the driving liquid to be injected into the microchip 1 can be maintained within a predetermined range, irrespective of variations of the liquid temperature and the characteristic of the micro pump MP. According to the abovementioned facts, it becomes possible to conduct a predetermined liquid conveying operation without generating errors in the timing of feeding the liquid to the predetermined section residing within the microchip 1, and without generating errors of the liquid conveyance controlling operation, such as a liquid amount, a changing rate of liquid amount, etc.

Figure 11:
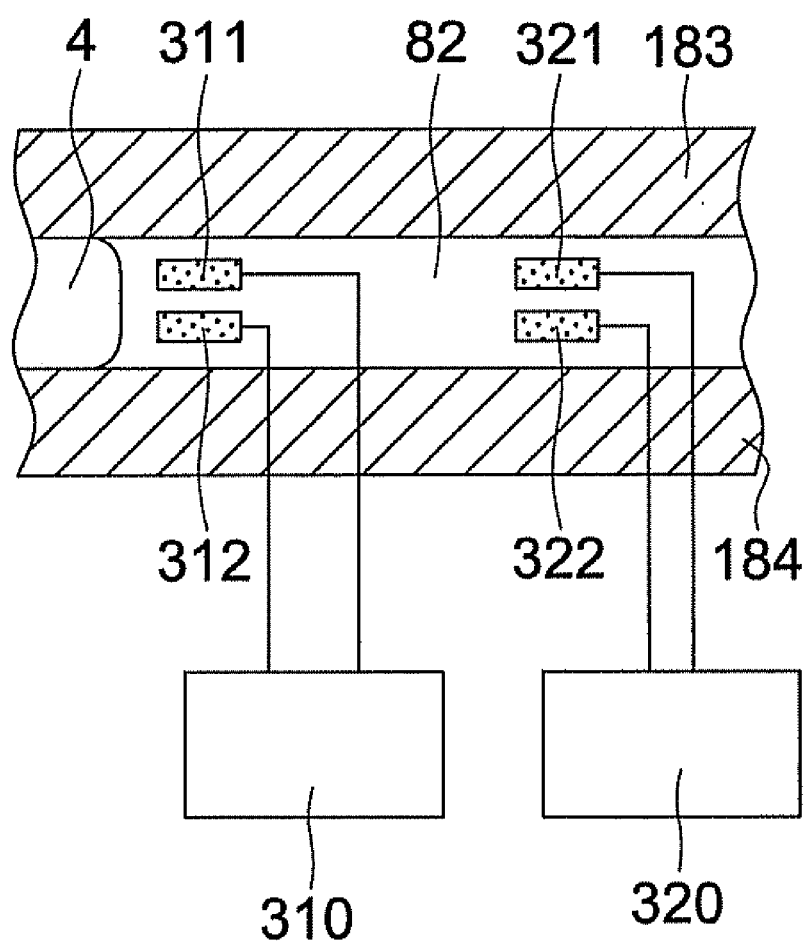
FIG. 11 shows a cross sectional schematic diagram indicating an example of a driving liquid detecting device employed in a microchip inspection system, embodied in the present invention as the second embodiment.
Figure 12:
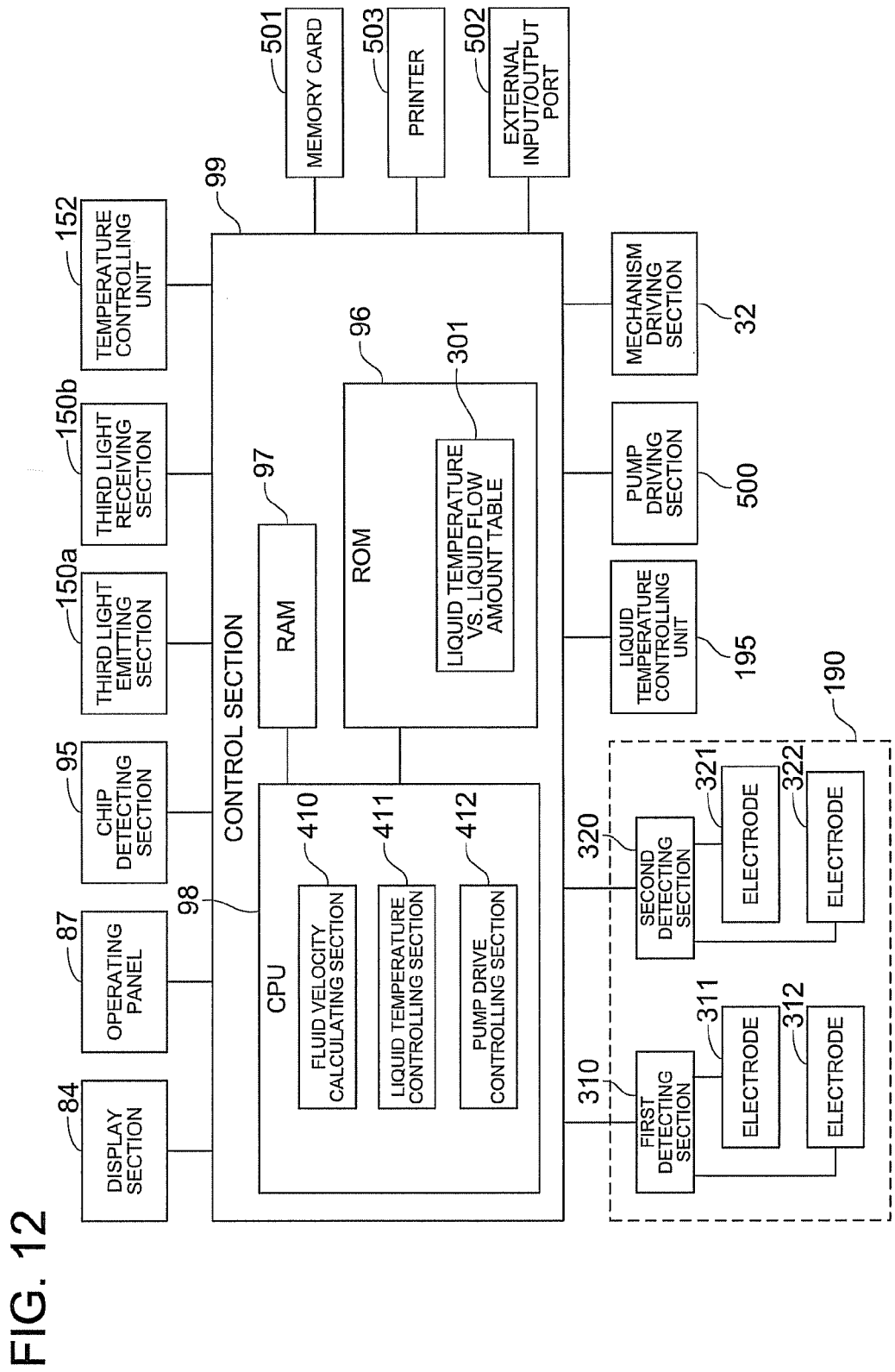
FIG. 12 shows a circuit block diagram of a reaction detecting apparatus in the second embodiment.

Next, referring to FIG. 11 and FIG. 12, the driving liquid detecting device 190 to be employed in the microchip inspection system 80, embodied in the present invention as the second embodiment, will be detailed in the following. FIG. 11 shows a cross sectional schematic diagram indicating an example of the driving liquid detecting device 190 employed in the microchip inspection system 80, embodied in the present invention as the second embodiment. FIG. 12 shows a circuit block diagram of the reaction detecting apparatus 82 in the second embodiment. In the following, the number same as that of the element previously explained is attached to an element same as the element previously explained, and the explanation of that will be omitted.

The driving liquid detecting device 190 of the second embodiment is constituted by the first detecting section 310 and the second detecting section 320, each of which is provided with a pair of electrodes, which is fixed onto the inner wall of the intermediate liquid flow path 182 and between which a voltage is applied, so as to detect the driving liquid based on a change of the electric current flowing between the electrodes when the driving liquid contacts the electrodes. The first detecting section 310 incorporates a power source for applying the voltage between an electrode 311 and an electrode 312, and an electronic circuit for detecting the electric current flowing between the electrode 311 and the electrode 312, so as to output a detection signal when the electric current exceeds a predetermined value. As well as the above, the second detecting section 320 incorporates a power source for applying the voltage between an electrode 321 and an electrode 322, and an electronic circuit for detecting the electric current flowing between the electrode 321 and the electrode 322, so as to output a detection signal, when the electric current exceeds a predetermined value due to the passage of the driving liquid.

As shown in FIG. 12, the detection signals, outputted by the first detecting section 310 and the second detecting section 320, are inputted into the CPU 98.

The processes, according to the inspection procedure to be conducted by the reaction detecting apparatus 82, are conducted in the same manner as in the procedure described previously by referring to FIG. 8, FIG. 9 and FIG. 10.

According to the second embodiment, since the electrodes can be fixed onto the inner wall of the intermediate liquid flow path 182, it becomes possible not only to widen the layout design flexibility, but also to apply it to an opaque liquid flow path.

As described in the foregoing, according to the present invention, it becomes possible not only to correct the influence of the viscosity change of the liquid, but also to provide a microchip inspection system, which makes it possible to accurately conduct the liquid conveyance controlling operation, and a program to be employed for the microchip inspection system.

While the preferred embodiments of the present invention have been described using specific term, such description is for illustrative purpose only, and it is to be understood that changes and variations may be made without departing from the spirit and scope of the appended claims.

What is claimed is:

1. A microchip inspection system for use with a driving liquid, the microchip inspection system comprising:
   a micro pump to inject the driving liquid from a liquid flow path into a microchip;
   a liquid temperature adjusting section to adjust a liquid temperature of the driving liquid;
   a driving liquid detecting section to detect presence or absence of the driving liquid at two predetermined positions located in the liquid flow path, so as to output detection signals;

a fluid velocity calculating section to calculate a fluid velocity based on the detection signals outputted by the driving liquid detecting section;

a liquid temperature controlling section to control the liquid temperature adjusting section, based on the fluid velocity calculated by the fluid velocity calculating section;

a driving liquid tank to store the driving liquid;

wherein the driving liquid tank is equipped with the liquid temperature adjusting section; and the liquid temperature adjusting section is structured to adjust the temperature of the driving liquid in the driving liquid tank while the driving liquid is in the driving liquid tank.

2. The microchip inspection system of claim 1, wherein the driving liquid detecting section is provided with:
- a light emitting section to irradiate light onto the liquid flow path in a direction orthogonal to the liquid flow path;
- a light receiving section to receive the light, irradiate by the light emitting section and penetrating through the liquid flow path, and to generate a signal corresponding to an amount of the light received; and
- a detecting section to compare the signal generated by the light receiving section with a predetermined value, so as to output the detection signal.

3. The microchip inspection system of claim 1, wherein the driving liquid detecting section is provided with:
- a pair of electrodes disposed inside the liquid flow path; and
- a detecting section to compare an electric signal, representing an electric current flowing between the pair of electrodes, with a predetermined value, so as to output the detection signal.

4. A computer readable medium storing a computer executable program for controlling a driving liquid to be introduced into a microchip, the program comprising program code for causing a computer to perform:

detecting presence or absence of the driving liquid by employing driving-liquid detecting devices disposed at two predetermined positions located in a mid-course of a liquid flow path led to the microchip, so as to output detection signals, before injecting the driving liquid into the microchip;

calculating a fluid velocity of the driving liquid currently flowing into the liquid flow path, based on the detection signals outputted in the detecting presence or absence of the driving liquid;

controlling a liquid temperature adjusting section to adjust a liquid temperature of the driving liquid, based on the fluid velocity calculated in the calculating a fluid velocity of the driving liquid;

injecting the driving liquid, the liquid temperature of which is adjusted by the liquid temperature adjusting section in the controlling a liquid temperature adjusting section, into the microchip; and storing the driving liquid into a driving liquid tank that is equipped with the liquid temperature adjusting section;

wherein the liquid temperature adjusting section is structured to adjust the temperature of the driving liquid in the driving liquid tank while the driving liquid is in the driving liquid tank.

* * * * *